(12) United States Patent
Suzuki et al.

(10) Patent No.: US 6,870,953 B2
(45) Date of Patent: Mar. 22, 2005

(54) METHOD OF SORTING OUT DEFECT-FREE WORKPIECE

(75) Inventors: Tetsuo Suzuki, Sayama (JP); Hideki Shigematsu, Sayama (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 553 days.

(21) Appl. No.: 09/788,648

(22) Filed: Feb. 21, 2001

(65) Prior Publication Data

US 2001/0033684 A1 Oct. 25, 2001

(30) Foreign Application Priority Data

Feb. 21, 2000 (JP) ........................................ 2000-043244

(51) Int. Cl.[7] .............................. G06K 9/00; G06K 9/68; B07C 5/06
(52) U.S. Cl. ........................ 382/152; 382/218; 209/619
(58) Field of Search ................................ 382/141, 152, 382/209, 217, 218; 348/86, 90–92, 125, 129, 130; 700/95, 117, 108–110, 174, 175; 702/34, 35; 76/101.1; 209/619, 620

(56) References Cited

U.S. PATENT DOCUMENTS

| | | | | |
|---|---|---|---|---|
| 3,625,357 A | * | 12/1971 | Ochs et al. | 209/625 |
| 3,743,091 A | * | 7/1973 | Fowlkes | 209/652 |
| 5,345,514 A | * | 9/1994 | Mahdavieh et al. | 382/152 |
| 5,388,707 A | * | 2/1995 | Stivison et al. | 209/602 |
| 5,823,356 A | * | 10/1998 | Goodrich et al. | 209/601 |

\* cited by examiner

*Primary Examiner*—Mehrdad Dastouri
*Assistant Examiner*—Virginia Kibler
(74) *Attorney, Agent, or Firm*—Birch, Stewart, Kolasch & Birch, LLP

(57) ABSTRACT

A method sorts out defect-free elements blanked out of a metal sheet for a belt for use in a continuously variable transmission. Each of the elements has a body and a head joined to the body with a pair of recesses defined therebetween. The elements are stacked in a transverse direction thereof into an annular form and bundled together by an assembly of stacked endless metal rings inserted in the recesses into a belt for use in a continuously variable transmission. The elements are inserted into a passage having a predetermined width to sort out and deliver those elements which have passed through the passage to a feed path. Respective images of the elements which have been delivered to the feed path are analyzed while in the feed path to compare the images with a reference element image. Elements which have entrapped foreign matter, outer profile deformations, and defects are rejected from the feed path, and other elements are fed through the feed path. The fed elements are stacked and arrayed in a transverse direction thereof downstream of the feed path. The arrayed elements are passed through gages having a shape complementary to a required shape for the recesses of the elements, and those elements which have passed through the gage are sorted out as defect-free elements.

11 Claims, 5 Drawing Sheets

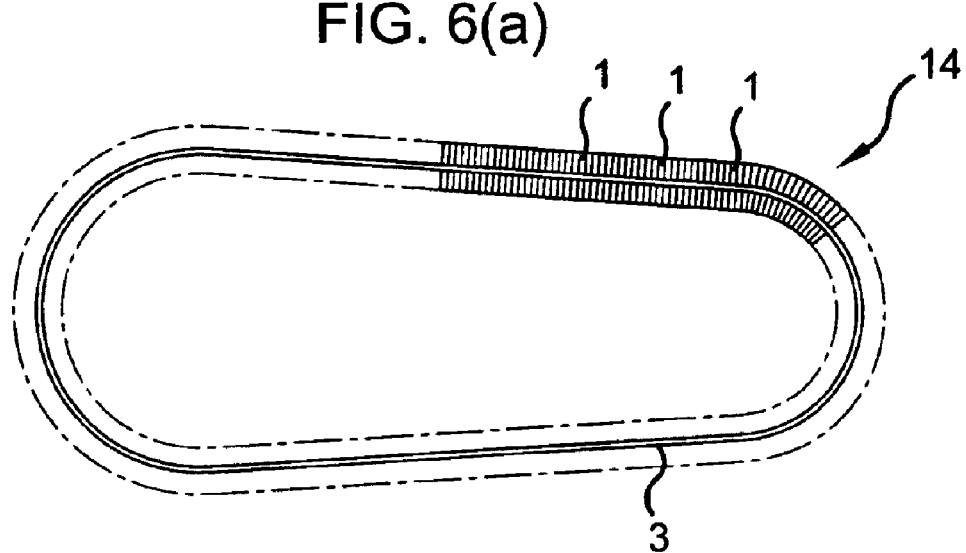
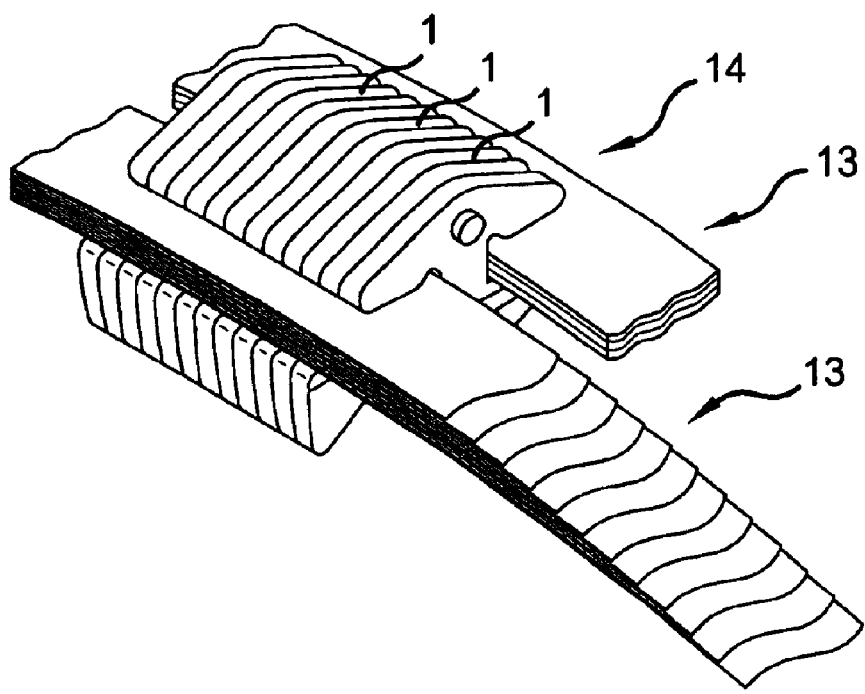

METHOD OF SORTING OUT DEFECT-FREE WORKPIECE

BACKGROUND OF THE INVENTION

1. Field of the Invention

The present invention relates to a method of sorting out defect-free workpieces blanked out of a metal sheet, and more particularly to a method of sorting out defect-free elements of a belt for use in a continuously variable transmission for automobiles.

2. Description of the Related Art

Continuously variable transmissions for use on automobiles employ an endless belt comprising a plurality of elements, each blanked out of a metal sheet, stacked in their transverse direction into an annular form and put together by endless rings.

As shown in FIG. 1 of the accompanying drawings, each of such elements, denoted by 1, comprises a body 2 and a head 5 joined to the body 2 with recesses 3, 4 defined therebetween. The body 2 has a pair of slanted edges 6, 7 on its lateral opposite sides which jointly provide a V-shaped surface for contacting a pulley of a continuously variable transmission. After the element 1 is blanked out of a metal sheet, the edges of the recesses 3, 4 and the slanted edges 6, 7 are ground by abrasive particles, and delivered by a belt conveyor or the like to a subsequent process where the element 1 is thermally treated. After a given number of elements 1 are thermally treated, they are stacked in their transverse direction into an annular form. Endless rings 13, each comprising a plurality of stacked sheet-like metal rings 12, are inserted in the respective recesses 3, 4 to bundle the elements 1 into a belt 14 for use in a continuously variable transmission.

When the element 1 is caught in a gap in the belt conveyor or thermally treated, the body 2 and the head 5 may possibly be strained or twisted. If the element 1 is strained or twisted, then when a plurality of elements 1 are stacked, the stacked elements 1 may become longer than a desired length or it may be difficult to insert the endless rings 13 into the recesses 3, 4.

When the element 1 is ground by abrasive particles or caught in a gap in the belt conveyor, the element 1 may possibly be damaged or partly broken off.

For inspecting elements 1, it has heretofore been customary for the worker to visually observe the elements 1 at the time the elements 1 are stacked. However, it is tedious and time-consuming to visually inspect all the elements 1 to be stacked. In addition, different inspection personnel have different standards for sorting out defect-free elements 1, and the manual inspection process may possibly overlook damaged or broken regions of elements 1.

SUMMARY OF THE INVENTION

It is therefore an object of the present invention to provide a method of easily and reliably sorting out defect-free workpieces blanked out of a metal sheet, particularly defect-free elements of a belt for use in a continuously variable transmission.

To achieve the above object, there is provided in accordance with the present invention a method of sorting out defect-free workpieces blanked out of a metal sheet, comprising the steps of inserting the workpieces into a passage having a predetermined width to sort out those workpieces which have passed through the passage, analyzing respective images of the workpieces which have passed through the passage to compare the images with a reference workpiece image, reject workpieces which have a portion different from the reference workpiece image, and sort out other workpieces, and applying a gauge having a shape complementary to a required shape for a functional portion of the workpieces, to the workpieces which have been sorted out, and sorting out those workpieces whose functional portion has a shape complementary to the shape of the gauge, as defect-free workpieces.

More specifically, there is provided in accordance with the present invention a method of sorting out defect-free elements blanked out of a metal sheet, each having a body and a head joined to the body with a pair of recesses defined therebetween, the elements being stacked in a transverse direction thereof into an annular form and bundled together by an assembly of stacked endless metal rings inserted in the recesses into a belt for use in a continuously variable transmission, the method comprising the steps of inserting the elements into a passage having a predetermined width to sort out and deliver those elements which have passed through the passage to a feed path, analyzing respective images of the elements which have been delivered to the feed path while in the feed path to compare the images with a reference element image, reject elements which have a portion different from the reference element image, and feed other elements, stacking and arraying the fed elements in a transverse direction thereof downstream of the feed path, and passing the arrayed elements through a gauge having a shape complementary to a required shape for the recesses of the elements, and sorting out those elements which have passed through the gauge as defect-free elements.

Defects of elements are mostly strains caused when the elements are fed to a subsequent process after they have been blanked out of a metal sheet and outer profile deformations such as twists of the body and head. Other defects include entrapped foreign matter such as abrasive particles used to grind the elements, and partial broken-off regions. Least frequent defects include outer profile deformations of the recesses such as protrusions projecting from the body and head into the recesses.

According to the present invention, an element (workpiece) blanked out of a metal sheet is passed transversely into the passage having a predetermined width to inspect strains and twists. If the element suffers a strain and/or a twist, then when a plurality of elements are stacked in their transverse direction, the element with a strain and/or a twist is spaced from adjacent elements by a large distance. The width of the passage is set to an allowable maximum value for the distance between adjacent elements. When an element whose strain and/or twist is greater than a certain reference size, the element inserted into the passage in a direction parallel to the transverse direction thereof cannot pass through the passage and is rejected. As a result, only those elements that can pass through the passage are sorted out and delivered to the feed path.

While being delivered through the feed path, an element is imaged, and the image is analyzed. The image is compared with a reference element image, and if the element has a portion different from the reference element image, then the element is rejected from the feed path. The step of analyzing respective images of the elements may comprise the steps of converting the images of the elements into respective binary images each having a predetermined number of pixels in a unit area, comparing the binary images with the reference element image, rejecting workpieces which have a portion different from the reference element image, and feeding other elements.

The portion different from the reference element image may be either entrapped foreign matter, an outer profile deformation, or a defect, for example. Entrapped foreign matter is determined by, for example, converting the image of the element into a binary image having a predetermined number of pixels in a unit area, comparing the binary image with the reference element image, and detecting a portion different from the reference element image. An outer profile deformation is determined by, for example, converting the image of the element into a binary image having a predetermined number of pixels in a unit area, calculating the position of the center of gravity from the number and positions of pixels of the image of the element, and comparing the calculated position of the center of gravity with the position of the center of gravity of a reference element. A defect is determined by, for example, converting the image of the element into a binary image having a predetermined number of pixels in a unit area, comparing the binary image with the reference element image, detecting a portion different from the reference element image, and counting the pixels of the defect to determine whether the size of the defect falls in an allowable range or not.

As a result, those elements which suffer entrapped foreign matter, an outer profile deformation, or a defect are rejected from the feed path, and other elements are discharged from the feed path, and stacked and arrayed in their transverse direction downstream of the feed path.

The arrayed elements are then inserted in the transverse direction into gauges which have a shape complementary to a desired shape for the recesses. Those elements which have protrusions extending from the body and head into the recesses cannot pass through the gauges and are detected as defective elements. Only those elements whose recesses have a shape complementary to the gauges can pass through the gauges, and are sorted out as defect-free elements.

According to the present invention, since elements that have cleared all the inspecting steps described above are sorted out as defect-free elements, the elements can be sorted out easily and reliably. Furthermore, because elements are inspected for defects successively from most to less frequent types, defect-free elements can be sorted out efficiently.

The above and other objects, features, and advantages of the present invention will become apparent from the following description when taken in conjunction with the accompanying drawings which illustrate a preferred embodiment of the present invention by way of example.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIGS. 6(a) and 6(b) are views showing a belt for use in a continuously variable transmission.

DETAILED DESCRIPTION OF THE PREFERRED EMBODIMENT

Figure 1:
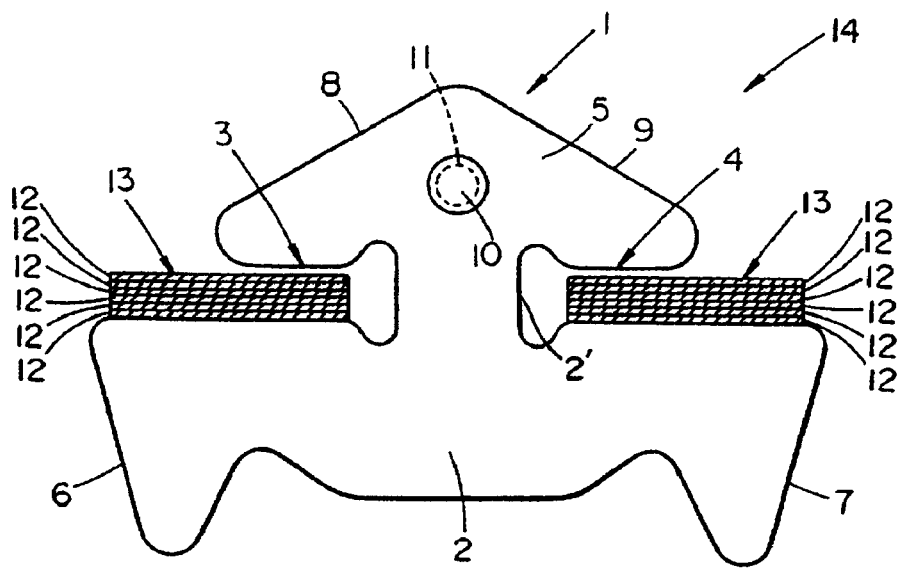
FIG. 1 is a plan view of an element as a workpiece to be sorted out by a method according to the present invention.

A method of sorting out defect-free workpieces according to the present invention is applicable to various workpieces blanked out of metal sheets. As shown in FIG. 1, one example of such workpieces is an element 1 of a belt for use in a continuously variable transmission for automobiles. The element 1 comprises a body 2 and a head 5 joined to the body 2 by a connector 2' that is defined by and disposed between recesses 3, 4. The body 2 has a pair of slanted edges 6, 7 on its lateral opposite sides which jointly provide a V-shaped surface for contacting a pulley of a continuously variable transmission. The head 5 also has a pair of slanted edges 8, 9 that are tapered toward its distal end. The head 5 has a dimple 10 positioned substantially centrally on one surface thereof and projecting from the surface in the transverse direction thereof, and a hole 11 defined in the other surface thereof in alignment with the dimple 10. When a plurality of elements 1 are stacked in their transverse direction, the dimples 10 of the elements 1 are fitted in the holes 11 in the adjacent elements 1 to position the elements 1 relatively to each other.

After the element 1 is blanked out of a metal sheet, the edges of the recesses 3, 4 and the slanted edges 6, 7 are ground by abrasive particles such as glass beads, and delivered by a belt conveyor or the like to a subsequent process where the element 1 is thermally treated.

After a given number of elements 1 are thermally treated, they are stacked in their transverse direction into an annular form. Endless rings 13, each comprising a plurality of stacked sheet-like rings 12, are inserted in the respective recesses 3, 4 to bundle the elements 1 into a belt 14 for use in a continuously variable transmission.

If the elements 1 include a defective element or elements, then it may be difficult to insert the endless rings 13 into the recesses 3, 4. Therefore, before the elements 1 are stacked together, all of the elements 1 are inspected.

Figure 2:
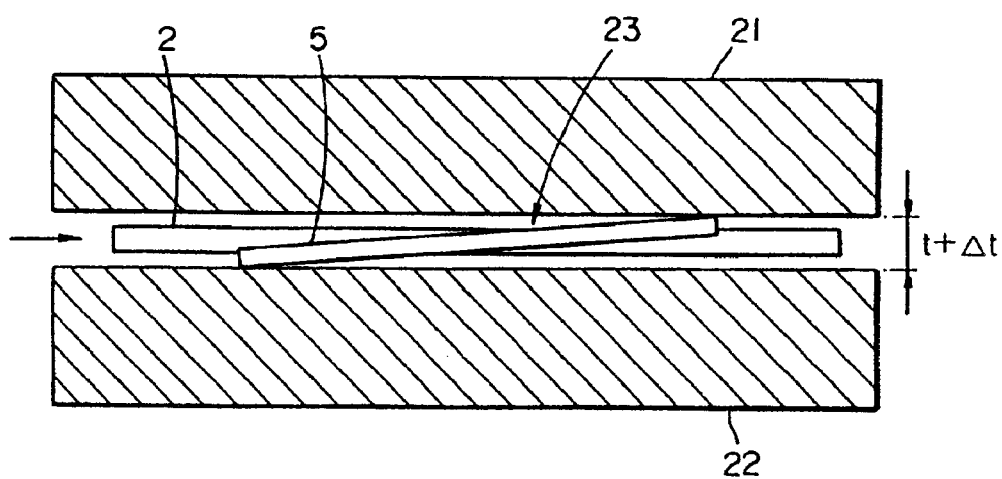
FIG. 2 is a cross-sectional view of a passage that is used in the method according to the present invention.

According to the present invention, all of the elements 1 are inspected as follows:

As shown in FIG. 2, the thermally treated element 1 is inserted transversely into a passage 23 that is defined between gates 21, 22. The passage 23 has a width which is set to a maximum value allowable as a distance between adjacent elements 1 when a plurality of elements 1 are stacked in their transverse direction, e.g., a width (t+Δt) which is slightly greater than the thickness t of the element 1.

If an element 1 blanked out of a metal sheet is strained or twisted at its body 2 and head 5 when the element 1 is caught by a belt conveyor on its travel to a subsequent process or subsequently thermally treated, then the element 1 cannot enter the passage 23, or cannot pass through the passage 23 due to contact with the gates 21, 22 even if the element 1 has entered the passage 23, as shown in FIG. 2. In FIG. 2, the element 1 is shown as twisted at the body and head 5.

If the element 1 that has entered the passage 23 is contacted by the gates 21, 22 and stopped in the passage 23, then upon elapse of a predetermined period time from after the element 1 has stuck, the gates 21, 22 are displaced away from each other, and a slit (not shown) is opened at the bottom of the passage 23. The stopped element 1 then drops from the passage 23 through the slit, and is rejected as a defective element.

An element 1 which is neither strained nor twisted or strained or twisted within an allowable range passes through the passage 23, and is delivered to a feed path, not shown. The feed path is arranged to feed elements 1, lying flatwise, one by one, and is associated with a camera.

The camera captures an image of an element 1 which is being fed through the feed path, and a controller (not shown) converts the image captured by the camera into a digital binary image. The digital binary image has a predetermined number of pixels within a unit area. Each of the pixels may have a given gradation.

Then, the controller compares the digital binary image with a reference element image to detect any entrapped foreign matter, outer profile deformations, and defects.

An element 1 may possibly entrap abrasive particles such as glass beads when it is ground. If the digital binary image of the element 1 includes a portion greater than the reference element image, then the controller determines that the element 1 has entrapped foreign matter such as an abrasive particle or particles.

Figure 3A:
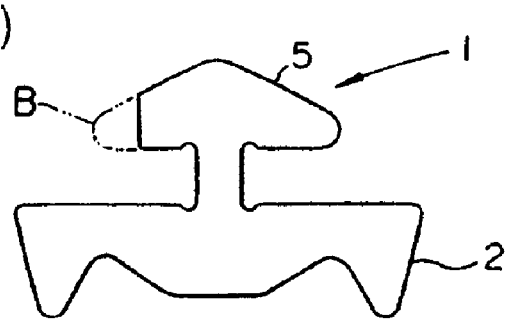
FIGS. 3(a) through 3(d) are plan views showing, by way of example, defective workpieces that are detected by an image analysis in the method according to the present invention.
Figure 3B:
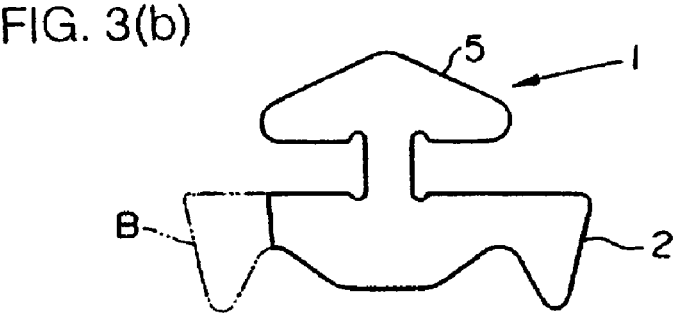
Figure 3C:
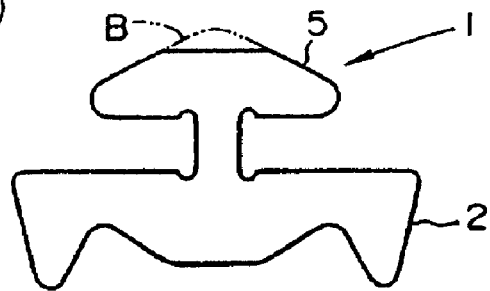
Figure 3D:
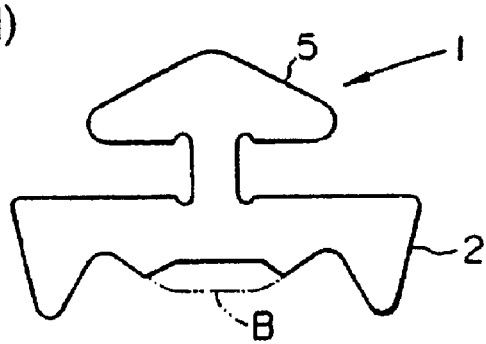

An element 1 may be broken off as indicated by the imaginary line B in FIG. 3(a) when it is blanked out of a metal sheet or gets caught by a belt conveyor on delivery to a subsequent process. An element 1 may be broken off at a side of the head 5 as shown in FIG. 3(a), at a side of the body 2 as shown in FIG. 3(b), at an upper end of the head 5 as shown in FIG. 3(c), or at a lower end of the body 2 as shown in FIG. 3(d). Alternatively, an element 1 may be broken off simultaneously at these spots.

The broken-off region B is judged as an outer profile deformation if the position of the center of gravity that is calculated from the number and positions of the pixels of the digital binary image is not the same as the position of the center of gravity of a reference element.

Figure 4:
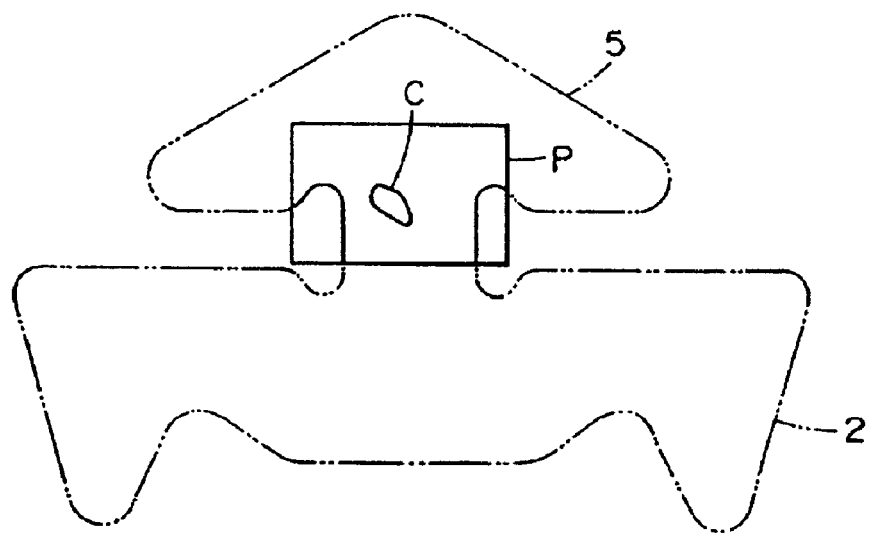
FIGS. 4(a) and 4(b) are plan views showing, by way of example, other defective workpieces that are detected by an image analysis in the method according to the present invention.
Figure 4:
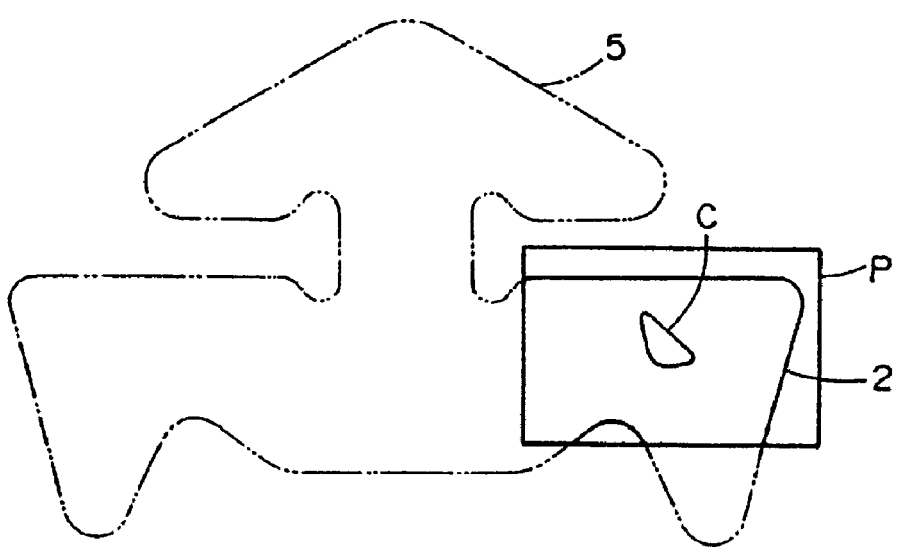

An element 1 may be damaged as indicated by a recess C in its surface in FIGS. 4(a) and 4(b) due to contact with foreign matter. In FIGS. 4(a) and 4(b), a portion of the element 1 is represented by a digital binary image P. The damage C is judged as a defect if the number of pixels included in the damage C in the image P is greater than a predetermined reference value.

If an element 1 is determined as suffering entrapped foreign matter, an outer profile deformation, or a defect in the feed path, then the element 1 is rejected as a defective element from the feed path. The feed path may be associated with one or more cameras. However, a plurality of cameras should preferably be used as they allow the outer surfaces of the element 1 to be accurately recognized by imaging the element 1 in different directions.

Figure 5:
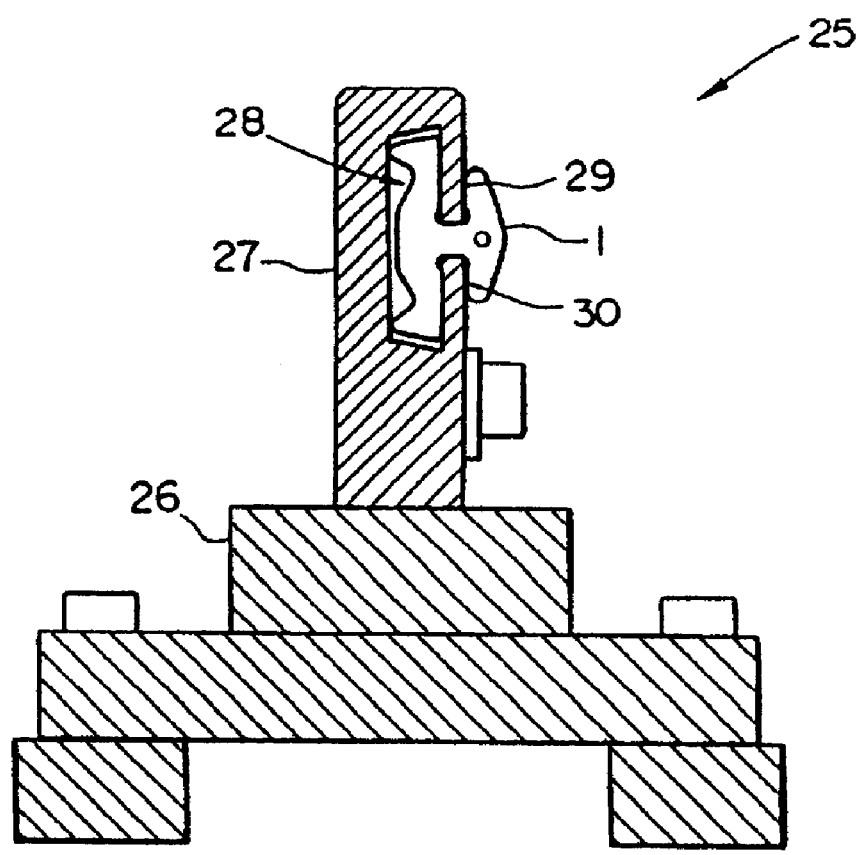
FIG. 5 is a cross-sectional view of a recess inspecting device used in the method according to the present invention.

Elements 1 that are not rejected from the feed path are discharged downstream of the feed path, and stacked and arrayed in their transverse direction each time a predetermined number of elements 1 for use in a belt 14 are produced. The arrayed elements 1 are then inserted in their transverse direction into a recess inspecting device 25 shown in FIG. 5. The recess inspecting device 25 comprises an inspection unit 27 mounted on a mount base 26. The inspection unit 27 has a through hole 28 for the insertion therethrough of the bodies of the arrayed elements 1 and a pair of gauges 29, 30 each having a shape complementary to a desired shape of one of the recesses 3, 4. If an element 1 has protrusions extending from the body 2 and the head 5 into the recesses 3, 4, then such protrusions are contacted by the gauges 29, 30 and hence the element 1 cannot pass through the inspection unit 27.

As a result, only an element 1 which is free of such protrusions and whose recesses 3, 4 are shaped complementarily to the gages 29, 30 can pass through the recess inspecting device 25. The element that has passe d through the recess inspecting device 25 is finally sorted out as a defect-free element because it has passed through the passage 23 and cleared the inspection based on an image analysis carried out in the feed path.

If an element 1 that cannot pass through the recess inspecting device 25 is included in the elements 1 arrayed for use in a belt 14 and inspected by the recess inspecting device 25, then that element 1 is rejected and replaced with an element 1 that has been judged as a defect-free element and supplied from a stock. Therefore, the arrayed elements 1 including the replacing element 1 can be used to manufacture a belt 14.

Although a certain preferred embodiment of the present invention has been shown and described in detail, it should be understood that various changes and modifications may be made therein without departing from the scope of the appended claims.

What is claimed is:

1. A method of sorting out defect-free workpieces blanked out of a metal sheet, comprising the steps of:

inserting the workpieces into a passage having a predetermined width to sort out those workpieces which have passed through said passage;

analyzing respective images of the workpieces which have passed through said passage to compare the images with a reference workpiece image, reject workpieces which have a portion different from said reference workpiece image, and sort out other workpieces; and applying a gauge having a shape complementary to a required shape for a functional portion of the workpieces, to the workpieces which have been sorted out, and sorting out those workpieces whose functional portion has a shape complementary to the shape of said gauge, as defect-free workpieces, wherein said step of applying a gauge, further comprises the step of inserting a pair of gauge portions of said gauge into respective recesses formed in the workpieces, said recesses being formed between a body and a head of the workpieces.

2. The method according to claim 1, wherein said step of analyzing respective images of the workpieces inserted into the passage comprises the steps of:

converting the images of the workpieces into respective binary images each having a predetermined number of pixels in a unit area, comparing the binary images with said reference workpiece image, reject workpieces which have a portion different from said reference workpiece image, and sort out other workpieces.

3. The method according to claim 1, wherein in said step of inserting, workpieces that are smaller than said predetermined width are passed through said passage to a feed path, and workpieces that are larger than said predetermined width are rejected.

4. The method according to claim 3, wherein in said step of analyzing, workpieces that have passed through said passage to said feed path are analyzed, and the workpieces that are not rejected are passed through said feed path to said gauge.

5. The method according to claim 1, wherein said step of applying a gauge further comprises the step of inserting the body of the workpieces into a through hole formed adjacent to said pair of gauge portions.

6. A method comprising the steps of:

sorting out defect-free elements blanked out of a metal sheet, each having a body and a head joined to the body with a pair of recesses defined therebetween, the elements being stacked in a transverse direction thereof into an annular form and bundled together by an assembly of stacked endless metal rings inserted in said recesses into a belt for use in a continuously variable transmission;

inserting the elements into a passage having a predetermined width to sort out and deliver those elements which have passed through said passage to a feed path;

analyzing respective images of the elements which have been delivered to said feed path while in said feed path to compare the images with a reference element image, reject elements which have a portion different from said reference element image, and feed other elements;

stacking and arraying the fed elements in a transverse direction thereof downstream of said feed path; and passing the arrayed elements through a gauge having a shape complementary to a required shape for the recesses of the elements, and sorting out those elements which have passed through said gauge as defect-free elements.

7. The method according to claim 6, wherein said step of analyzing respective images of the elements comprises the steps of:

converting the images of the elements into respective binary images each having a predetermined number of pixels in a unit area, comparing the binary images with said reference element image, rejecting workpieces which have a portion different from said reference element image, and feeding other elements.

8. The method according to claim 6, wherein said portion different from said reference element image is either entrapped foreign matter, an outer profile deformation, or a defect.

9. The method according to claim 8, wherein said entrapped foreign matter comprises an abrasive particle used to grind an element.

10. The method according to claim 8, wherein said outer profile deformation comprises a partial broken-off region of an element.

11. The method according to claim 8, wherein said defect comprises a recess in a surface of an element.

* * * * *